United States Patent [19]

Mack

[11] Patent Number: 4,668,722
[45] Date of Patent: May 26, 1987

[54] HINDERED PIPERIDINOALCOHOL 1,1,1-TRIOXYALKANE STABILIZERS

[76] Inventor: Gerry P. Mack, 34-28 86th St., Jackson Heights, N.Y. 11372

[21] Appl. No.: 808,340

[22] Filed: Dec. 13, 1985

[51] Int. Cl.$^4$ ............ C08K 5/34; C08K 5/51; C07D 401/14; C07D 211/32
[52] U.S. Cl. .................. 524/103; 524/99; 524/117; 524/120; 524/128; 524/147; 524/151; 524/153; 524/133; 524/102; 546/188; 546/207; 546/216; 546/225
[58] Field of Search ............... 546/188, 207, 216, 223; 524/99, 102, 103, 117, 120, 128, 147, 151, 153, 133

[56] References Cited

U.S. PATENT DOCUMENTS 4,423,174 12/1983 Minagawa et al. ............... 546/188

*Primary Examiner*—Robert T. Bond

[57] ABSTRACT

New hindered piperidinoalcohol 1,1,1-trioxyalkanes are disclosed. In the 1,1,1-trioxyalkanes, at least on 1,1,1-trioxyalkane group is linked to the residue of an alcohol linked to the 4-position of a 2,2,6,6-tetraalkylpiperidine compound having 12 to 75 carbon atoms. For each 1,1,1-trioxalkane group, there are 1 to 3 tetraalkylpiperidine groups. The alkyl groups linked to the piperidine ring have from one to five carbon atoms each. The fourth substituent on the carbon atom of the 1,1,1-trioxyalkane is a hydrogen atom or an aliphatic group having one to five carbon atoms.

The disclosed 1,1,1-trioxyalkanes protect a variety of synthetic resins against the deteriorative effects of exposure to actinic light.

Stabilizer compositions comprising a disclosed 1,1,1-trioxyalkane and a known polymer stabilizer, as well as synthetic resin compositions stabilized with such stabilizer compositions, are also disclosed.

40 Claims, No Drawings

HINDERED PIPERIDINOALCOHOL 1,1,1-TRIOXYALKANE STABILIZERS

BACKGROUND OF INVENTION

1. Field of the Invention

This invention relates to novel 1,1,1-trioxyalkanes capable of stabilizing synthetic resin compositions against the deleterious effects of actinic light, to stabilizer compositions comprising these 1,1,1-trioxyalkanes, and to stabilized synthetic resin compositions in which a stabilizing quantity of such 1,1,1-trioxyalkanes are incorporated. More particularly, the invention relates to novel 1,1,1-trioxyalkanes of sterically hindered piperidino alcohols, that is 1,1,1-trioxyalkanes of alcohols in which the alcohol group is linked to the 4-position of the piperidine ring in a 2,2,6,6-tetraalkylpiperidine compound.

2. Prior Art

A multitude of sterically hindered piperidine compound stabilizers has been disclosed, following upon the pioneer disclosure by K. Murayama et al in U.S. Pat. No. 3,640,928 of Feb. 8, 1972. Murayama et al disclosed the stabilization of synthetic polymers against photo- and thermo-deterioration by incorporating therein, in a sufficient amount to prevent such deterioration, a piperidine derivative having the general formula

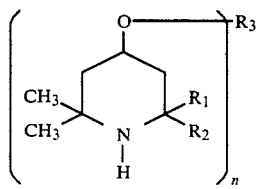

or a salt thereof.

In the above formula I:

$R_1$ and $R_2$, which may be the same or different, each are an alkyl group such as methyl, ethyl, isopropyl or dodecyl, or they form, together with the carbon atom to which they are attached, a saturated alicyclic group such as

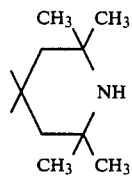

or a group of the formula

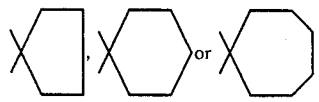

n is an integer of 1 to 3 inclusive; and when n is 1, $R_3$ is an acyl group derived from an aliphatic, alicyclic or heterocyclic monocarboxylic acid; an N-substituted carbamoyl group derived from an n-substituted carbamic acid; an N-substituted thiocarbamoyl group derived from an N-substituted thiocarbamic acid; a monovalent group obtained by removing a hydroxyl group from an oxoacid; an alkyl group; a cycloalkyl group; an aralkyl group; an aryl group; or a group of the general formula

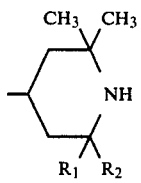

(wherein $R_1$ and $R_2$ are as defined above);

when n is 2, $R_3$ is a diacyl group derived from an aliphatic, alicyclic, aromatic or heterocyclic dicarboxylic acid; a dicarbamoyl group derived from dicarbamic acid; a bisthiocarbamoyl group derived from bisthiocarbamic acid; a carbonyl group; a divalent group obtained by removing two hydroxyl groups from an oxacid; an alkylene group; an arylene group; or an arylenedialkylene group; and when n is 3, $R_3$ is a triacyl group derived from an aliphatic, alicyclic, aromatic or heterocyclic tricarboxylic acid; a tricarbamoyl group derived from tricarbamic acid; a tristhiocarbamoyl group drived from tristhiocarbamic acid; a trivalent group obtained by removing three hydroxyl groups derived from an oxacid; an alkanetriyl group; arenetriyl group; or an arenetriyltrialkylene group.

In U.S. Pat. No. 3,840,494 of Oct. 8, 1974, Murayama et al disclosed as stabilizers acid esters of 4-piperidinol derivatives having the formula

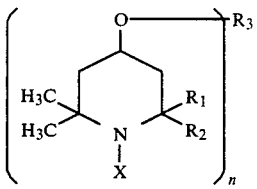

wherein $R_1$ and $R_2$ may be the same or different and represent an alkyl group of 1 to 4 carbon atoms or they may form, together with the carbon atom to which they are attached, a saturated alicyclic group or the group of the formula

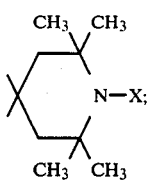

X is hydrogen atom, oxygen free radical (—O) or an alkyl group of 1 to 4 carbon atoms;

n is an integer of 1 through 4 inclusive; and $R_3$ represents, when n is 1, an acyl group derived from an aliphatic or aromatic monocarboxylic acid, when n is 2, a diacyl group derived from an aliphatic or aromatic dicarboxylic acid or carbonyl group, when n is 3, a triacyl group derived from an aliphatic or aromatic tricarboxylic acid or a trivalent group obtained by eliminating three hydroxyl groups from phosphoric acid, phosphorous acid or boric acid, and when n is 4, a tetraacyl group derived from an aromatic tetracarboxylic acid or a tetravalent group obtained by eliminating four hydroxyl groups from orthosilicic acid, and also disclosed a process which comprises reacting a 4-piperidinol derivative having the formula

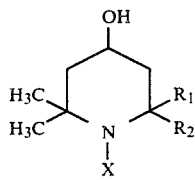

wherein $R_1$ and $R_2$, and X have the same meanings as above with a lower alkyl ester of an acid having the formula

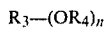

wherein $R_3$ and n have the same meanings as above and $R_4$ is a lower alkyl group, e.g., methyl, ethyl or propyl in the presence of an alcoholysis catalyst.

In U.S. Pat. No. 3,899,464 of Aug. 12, 1975, Murayama et al disclosed piperidine spiro comounds having the formula

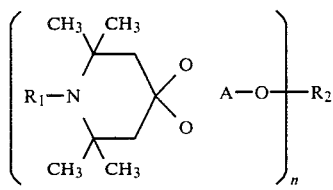

wherein $R_1$ represents hydrogen atom, an alkyl group, a substituted alkyl group, an alkenyl group, an alkenyl group, a substituted or unsubstituted aralkyl group, an aliphatic acyl group, an alkoxycarbonyl group or an aralkoxycarbonyl group, n is an integer of 1 to 4; when n is 1, $R_2$ represents hydrogen atom, an aliphatic, aromatic or heterocyclic monoacyl group, an alkyl group, an alkenyl group, an alkynyl group, an aralkyl group, an aryl group, an alkoxyalkyl group, an epoxyalkyl group, an alkoxysulfonylalkyl group, N-substituted carbamoyl group, a N-substituted thiocarbamoyl group, a monovalent group from an oxoacid or group

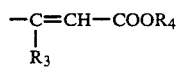

in which $R_3$ represents hydrogen atom, a lower alkyl group or phenyl group and $R_4$ represents an alkyl group; when n is 2, $R_2$ represents carbonyl group, an aliphatic or aromatic diacyl group, an alkylene group, an alkenylene group, an alkynylene group, an aralkylene group, a N-substituted dicarbamoyl group or a divalent group from an oxoacid; when n is 3, $R_2$ represents an aromatic triacyl group or a trivalent group from an oxoacid; and when n is 4, $R_2$ represents an aromatic tetraacyl group, and A represents a group

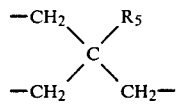

in which $R_5$ represents hydrogen atom or a lower alkyl group or, when n is 1, $R_5$ may represent toegether with $R_2$ a group

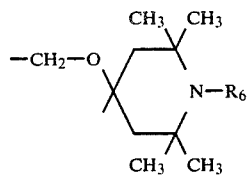

in which $R_6$ represents the same group as defined in $R_1$ and may be the same or different from $R_1$ or a group

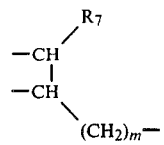

in which m is 1 or 2 and $R_7$ represents hydrogen atom or, when n and m are 1, $R_7$ represents methylene group together with $R_2$.

Esters of 2,2,6,6-tetraalkylpiperidine-4-alcohols in which the piperidine ring carries an additional hydrocarbon substituent on a ring carbon atom have been disclosed by N. Soma et al in U.S. Pat. No. 4,075.165 of Feb. 21, 1978.

Additional stabilizers characterized by 2,2,6,6-tetraalkylpiperidine structure connected through a 4-oxygen atom are disclosed in U.S. Pat. Nos. 4,021,432, 4,087,406, 4,096,114, 4,101,508, 4,102,858, 4,105,626, 4,110,305, 4,116,927, 4,128,608, 4,136,081, 4,136,083, 4,141,884, 4,148,783, 4,148,784, 4,154,722, 4,166,803, 4,177,186, 4,194,989, 4,197,236, 4,198,534, 4,210,578, 4,212,974, 4,221,704, 4,223,148, 4,231,921, 4,233,412, 4,234,699, 4,234,700, 4,250,268, 4,263,202, 4,265,805, 4,293,467, 4,293,468, 4,294,949, 4,308,362, 4,345,493, 4,360,675, 4,369,321, 4,377,690, and 4,378,443 as well as British Pat. No. 1,588,259 and British published patent application No. 2,014,586 among others.

There have also been disclosures of 2,2,6,6-tetraalkylpiperidine derivative stabilizers in which a subsituent is connected to the 4-position of the piperidine ring through carbon (see U.S. Pat. Nos. 3,474,608 and 4,130,710) or through nitrogen (see U.S. Pat. Nos. 3,684,765, 3,925,376, and 4,104,248).

Polymeric stabilizers in which a 2,2,6,6-tetraalkylpiperidine structure is connected through a 4-oxygen on the piperidine ring have been disclosed. The tetraalkylpiperidine structure can be part of the polymeric chain or can occur as a side-chain substituent in a regular or randomly repeating manner. Representative disclosures include J. Rody et al U.S. Pat. Nos. 4,233,412, 4,234,700 and 4,250,268; N. Kubota et al, U.S. Pat. No. 4,413,076; and F. Fu et al U.S. Pat. No. 4,413,096. In much of the voluminous art summarized above, there appear statements to the effect that previously known 2,2,6,6-tetraalkylpiperdine compound stabilizers are unsatisfactory, as illustrated by the following, quoted from Kubota et al:

2,2,6,6-Tetraalkyl piperidine compounds do not impart color to the polymer, and act as quenchers. However, the available piperidine compounds are unsatisfactory in stabilizing effectiveness, are so volatile that they are lost when the polymer is heated at elevated temperatures, and are extracted by water.

2,2,6,6-Tetraalkyl piperidine compounds of high molecular weight are said to have improved properties in these respects. Several types of polymers have been dscribed. Polyesters containing hindered piperidyl groups in the molecule are proposed in Japanese patent publication Kokai No. 141,883/77. Acrylate polymers containing hindered piperidyl groups are proposed in Japanese patent publication Kokai No. 157,612/80. While the volatility of these compounds is low, their stabilizing effectiveness is unsatisfactory.

Nevertheless, the market for stabilizers that do not impart color remains dominated by the earliest introduced products, in particular the compound bis(2,2,6,6-tetramethylpiperidin-4-yl)sebacate of Murayama et al U.S. Pat. No. 3,640,928. In spite of its bulk, therefore, the art is not helpful to the polymer user in search of better stabilization against the deteriorative effects of exposure to active light. Orthoformate esters as a class have been known for over a century. For a review of methods of preparation and interconversion of orthoformates, the article by R. H. DeWolfe, *Synthesis* 1974, pages 153-160 can be consulted. In particular, the author notes that transesterification of trimethyl and triethyl orthoformate occurs smoothly with most primary alcohols while transesterifications involving secondary alcohols are slow, and can remain incomplete.

G. Kesslin et al in U.S. Pat. No. 3,415,846 of Dec. 10, 1968 disclosed the reaction of a trialkyl orthoformate with a 1,1,1-tris(hydroxymethyl)alkane to give a bicyclic orthoformate such as 4-methyl-2,6,7-trioxabicyclo(2.2.2)octane.

L. L. Wood in U.S. Pat. No. 3,514,428 of May 26, 1970 disclosed orthoformate ester heat stabilizers for polyvinyl chloride resin, prepared by reaction of triethyl orthoformate with a higher alcohol such as benzyl alcohol. Similarly, G. Kesslin et al in U.S. Pat. No. 3,546,188 of Dec. 8, 1970 disclosed orthoformate esters such as triallyl orthoformate to be effective in polyvinyl chloride stabilization against deterioration under thermal stress. The orthoformate ester stabilizers disclosed by Wood and by Kesslin contained only carbon, hydrogen, and oxygen. I. Bechara et al in U.S. Pat. No. 3,879,456 of Apr. 22, 1975 disclosed aminoalkanol orthoformate ester activators for preparation of polyurethanes and cured epoxy resins, for example tris(2(dimethylamino)ethyl)orthoformate and bis(2-(dimethylamino)ethyl methyl orthoformate by reaction of trimethyl orthoformate with 2(dimethylamino)ethanol.

R. A. Swaringen, Jr. et al in Journal of Organic Chemistry, 1980, pages 3986–89, disclosed the reaction of orthoformate esters with cyclic amines at the ring nitrogen to give N-orthoamide such as tripiperidinomethane from piperidine and trimorpholinomethane from morpholine. N. Soma et al in U.S. Pat. Nos. 4,075,165 of Feb. 21, 1978 and 4,141,883 of Feb. 27, 1979 disclosed a different reaction of certain piperidine compounds with triethyl orthoformate. Soma et al disclosed that the piperidine compounds of formula (I), (II) or (III) wherein X represents a formyl group can be prepared by reacting a corresponding compound wherein X represents a hydrogen atom with ethyl orthoformate in the presence of an acid catalyst.

Soma's formulas (I), (II), and (III) refer to, respectively, Soma's 3- and/or 5-substituted-2,2,6,6,-tetrasubstituted-4-piperidinol derivative stabilizer and the substituted piperidin-4-one and piperidin-4-ol precursors thereof, as shown:

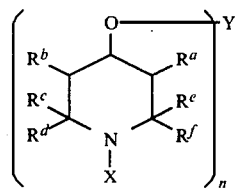

wherein:

$R^a$ and $R^b$ are the same or different and each represents a hydrogen atom, a lower alkyl group, an alkenyl group, an alkynyl group or an aralkyl group, provided that $R^a$ and $R^b$ do not simultaneously represent hydrogen atoms;

$R^c$ and $R^d$ are the same or differnet and each represents a lower alkyl group;

$R^3$ represents an alkyl group;

$R^f$ represents an alkyl group, a phenyl group, an aralkyl group or a 5- or 6-membered aromatic heterocyclic group containing an oxygen, sulphur or nitrogen atom; or $R^e$ and $R^f$, together with the carbon atom to which they are attached, represent a cycloalkyl group or a group of the formula:

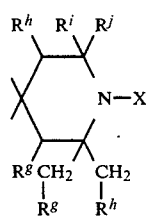

(wherein $R^g$ and $R^h$ are the same or different and each represents a hydrogen atom or a lower alkyl group, provided that $R^h$ does not represent a hydrogen atom when $R^g$ represents a lower alkyl group; $R^i$ and $R^j$ are the same or different and each represents a lower alkyl group; and X is as hereafter defined);

X represents a hydrogen atom, an oxyl radical, an alkyl group, an alkenyl group, an alkoxyalkyl group, an aralkyl group, which is unsubstituted or which has one or more substituents in its aryl moiety, a 2,3-epoxypropyl group, a group of formula —CH$_2$COOR$^1$ (wherein $R^1$ represents an alkyl group, an alkenyl group, a phenyl group, an aralkyl group or a cyclohexyl group), a group of formula:

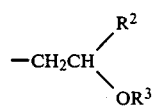

(wherein $R^2$ represents a hydrogen atom, a methyl group or a phenyl group and $R^3$ represents a hydrogen atom or an acyl group O, an aliphatic acyl group or a group of formula —COOR$^4$ (wherein R$^4$ represents an alkyl group, a benzyl group or a phenyl group); Y represents an organic or inorganic group or atom having a valency of from 1 to 4 and having essentially no adverse effect on the polymer stabilization activity; and n is an integer of from 1 to 4 inclusive,

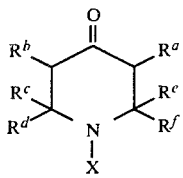

(wherein R$^a$, R$^b$, R$^c$, R$^d$, R$^e$, R$^f$ and X are as defined above, provided that X does not represent an oxyl radical),

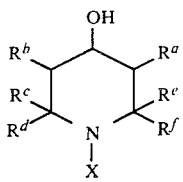

(wherein R$^a$, R$^b$, R$^c$, R$^d$, R$^e$, R$^f$ and X are as defined above).

SUMMARY OF THE INVENTION

In accordance with this invention, new 1,1,1-trioxyalkanes are prepared of an alcohol linked to the 4-position of the piperidine ring in a 2,2,6,6-tetraalkylpiperidine compound. The trioxyalkane is a single carbon atom linked to an aliphatic group or a hydrogen atom and three oxygen atoms, each of which is linked to an organic group through carbon; at least one such organic group is 2,2,6,6-tetraalkylpiperidine linked to the 1,1,1-trioxyalkane group through the 4-position of the piperidine ring. The 1,1,1-trioxyalkanes have 12 or more carbon atoms, one or more 1,1,1-trioxyalkane groups, one or more 2,2,6,6-tetraalkylpiperidine groups, and 1 to 4 carbon atoms in each alkyl group linked to a carbon atom of the piperidine ring in the 2,2,6,6-tetraalkylpiperdine compound. The 2,2,6,6-tetraalkylpiperidine group can carry additional alkyl groups on the piperidine ring, as at the 1,3 or 5 positions.

The 1,1,1-trioxyalkanes of this invention include trioxymethanes and higher 1,1,1-trioxyalkanes such as 1,1,1-trioxyethanes, 1,1,1-trioxybutanes, and 1,1,1-trioxyhexanes. Synthetic resin stabilizer compositions comprising the 1,1,1-trioxyalkanes of this invention contain at least one known polymer stabilizer along with one or more 1,1,1-trioxyalkanes according to this invention. The proportions of 1,1,1-trioxyalkane to known polymer stabilizer in such stabilizer compositions can range from 10:1 to about 1:10 by weight.

A variety of synthetic resins is stabilized against the deleterious effects of actinic light by incorporating with the resin 0.01 to about 2 parts by weight per 100 parts of synthetic resin of a 1,1,1-trioxyalkane according to this invention.

DESCRIPTION OF PREFERRED EMBODIMENTS

Essential to the achievement of the unexpected effectiveness in synthetic resin stabilizer compositions of the 1,1,1-trioxyalkanes of this invention are the presence in the molecule of both trioxyalkane and 2,2,6,6-tetraalkylpiperidine structures linked through the 4-position of the piperidine ring, and controlled molecular weight and polarity to maximize compatibility of the 1,1,1-trioxyalkane with a variety of synthetic resins and minimize the loss therefrom by migration, leaching, or evaporation. As a result, the stabilizing effectiveness of the 1,1,1-trioxyalkanes of this invention is maintained over long periods of time where resin compositions stabilized with the 1,1,1-trioxyalkanes are intermittently exposed to actinic light and also to the actions of air, water, and chemical solutions at an elevated temperature.

Preferred 1,1,1-trioxyalkanes according to this invention are represented by the formula:

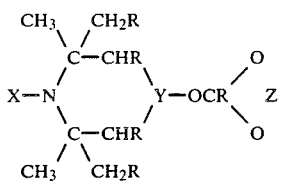

in which independently at each occurrence R is hydrogen or alkyl having 1 to 3 carbon atoms, X is hydrogen, oxyl radical O, alkyl having 1 to 22 carbon atoms, hydroxyalkylene having 2 to 6 carbon atoms, aliphatic acyloxyalkylene having 1 to 22 carbon atoms in the acyl group and 2 to 6 carbon atoms in the alkylene group, $C_mH_{2m}O—CH(OR')_2$ or $C_mH_{2m}O—CH(OR''O)$; R' is

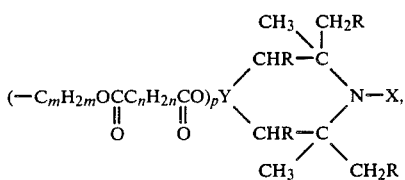

alkenyl having 3 to 22 carbon atoms, alkyl having 1 to 22 carbon atoms, hydroxyalkylene having 1 to 2 hydroxyl groups and 2 to 6 carbon atoms, aliphatic acyloxyalkylene having 1 to 22 carbon atoms in the acyl group and 2 to 6 carbon atoms in th akylene group; R'' is alkylene having 2 to 20 carbon atoms; Y is

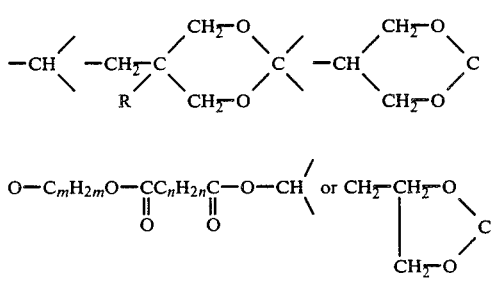

Z is selected from the group consisting of R' groups, R'' groups, and

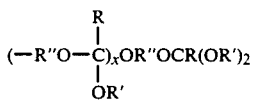

groups taken in sufficient number to satisfy the valences of the two 1,1,1-trioxyalkane oxygen atoms linked to Z; m is an integer from 2 to 10, n is an integer from 0 to 14, p is 0 or 1, and x is an integer from 0 to 10.

In this formula, R alkyl groups can be methyl, ethyl, propyl, and 1-methylethyl. X and R' alkyl groups can be R as well as t-butyl, sec-butyl, isobutyl, n-butyl, n-amyl, sec-amyl, t-amyl, neopentyl, 4-methyl-2-pentyl, 2-ethylbutyl, hexyl, sec-hexyl, n-heptyl, 2-heptyl, 4-heptyl, n-octyl, 2-ethylhexyl, iso-octyl, 2-ethyl-4-methylpentyl, 2-octyl, nonyl, 3,5,5-trimethylhexyl, isononyl, n-decyl, isodecyl, n-dodecyl, 2-butyloctyl, isotridecyl, tetradecyl, hexadecyl, 2-hexadecyl, n-octadecyl, eicosanyl, and docosanyl.

R' alkenyl groups can contain one or more ene linkages as in, for example, allyl, crotyl, methallyl, 2-hexen-1-yl, 2-ethyl-2-hexen-1-yl, 10-undecen-1-yl, oleyl, linoleyl, and erucyl.

Hydroxyalkylene groups at X and at R' can be, for example, 2-hydroxyethyl, 2-hydroxypropyl, 3-hydroxypropyl, 2,3-dihydroxypropyl, 4-hydroxybutyl, 3-hydroxypropyl, 2,3-dihydroxypropyl, 4-hydroxybutyl, 3-hydroxybutyl, 2,4-dihydroxybutyl, 3,4-dihydroxybutyl, 3-hydroxy-2,2-dimethylpropyl, 2,2-bis(hydroxymethyl)butyl, 2-hydroxypentyl, 5-hydroxypentyl, 5-hydroxy-3-methylpentyl, 6-hydroxyhexyl, and 5,6-dihydroxyhexyl.

Acyloxyalkylene groups at X and at R' can be any of the above hydroxyalkylene groups acylacted with an aliphatic acid having 1 to 22 carbon atoms. Hydroxyalkylene groups having two hydroxyl groups can be acylated at either or both of the hydroxy groups. The aliphatic acid can be saturated or unsaturated and can be monobasic or polybasic. When the aliphatic acid is a polybasic acid, the additional acid groups therein can be free carboxyl groups or esterified carboxylate ester groups. Saturated monobasic acids that can be used to generate acyloxyalkylene groups at X and at R' can be, for example, formic acid, acetic acid, propionic acid, isovaleric acid, 2-ethylbutyric acid, heptanoic acid, 2-ethylhexanoic acid, pelargonic acid, neodecanoic acid, capric acid, lauric acid, myristic acid, palmitic acid, stearic acid, and behenic acid. Unsaturated monobasic acids that can be used include, for example, acrylic acid, methacrylic acid, crotonic acid, 3,3-dimethylacrylic acid, 2-ethylhex-2-enoic acid, omega-undecylenic acid, oleic acid, linoleic acid, and erucic acid. Saturated polybasic acids that can be used include, for example, oxalic acid, succinic acid, glutaric acid, 2-methylglutaric acid, adipic acid, azelaic acid, 2,5-diethyladipic acid, sebacic acid, dodecandioic acid, butane-1,2,4-tricarboxylic acid, and butane-1,2,3,4-tetracarboxylic acid. Unsaturated polycarboxylic acids that can be used include maleic acid, fumaric acid, itaconic acid, aconitic acid, tripropylenesuccinic acid, dodecenylsuccinic acid, and octadecenylsuccinic acid. Aliphatic acyloxyalkylene groups resulting from the use of the recited acids with the recited hydroxyalkylene groups include, for example, 2-acetoxyethyl, 2,3-diacetoxypropyl, 2-lauroyloxyethyl, 6-succinoyoxyhexyl, 2-(9-methoxycarbonylnonanoyloxy)ethyl, and others that are readily apparent to one skilled in the art.

R" alkylene groups present in X or in the structure Z can be, for example 1,2-ethylene, 1,2-propylene, 1,3-propylene, 1,2-butylene, 1,3-butylene, 2,2-dimethyl-1,3-propylene, 2,3-butylene, 2-methyl-2,4-pentylene, 1,1-diethylethylene, 1-hexylethylene, 1-nonylethylene, 1-tetradecylethylene, and 1-octadecylethylene.

The structure Z in the 1,1,1-trioxyalkane is linked to two oxygen atoms of the trioxyalkane group, and is made up of as many groups as required to satisfy these two position linkages. Accordingly, Z can be two R' groups, which can be the same or different; Z can be two

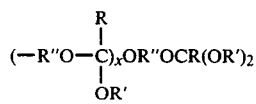

which can be the same or different; and can be one R' group and one

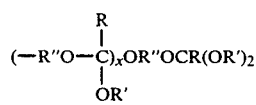

group. When Z is an R" group, there is only one such group linked to both oxygen atoms of the trioxyalkane group.

The hindered piperidinoalcohol 1,1,1-trioxyalkanes of this invention can be prepared by the reaction of a hindered piperidinoalcohol having an alcoholic hydroxyl group linked to the 4-position of a 2,2,6,6-tetraalkylpiperidine with a trioxyalkylating agent. This reaction of the trioxyalkylating agent links the 1,1,1-trioxyalkane group to the 4-position of the 2,2,6,6-tetraalkylpiperidine ring and introduces a Z structure into the molecule. Particular Z structures can be exchanged for other Z structures by subsequent reactions as required.

Many hindered piperidinoalcohols having an alcoholic hydroxyl group linked to the 4-position of a 2,2,6,6-tetraalkylpiperidine are known, and in some cases commercially available. Methods of preparation are illustrated by M. Minagawa et al. in U.S. Pat. No. 4,124,564 of Nov. 7, 1978 and Y. Nakahara et al. in U.S. Pat. No. 4,250,312 of Feb. 10, 1981, among others.

Trioxyalkylating agents that can be reacted with hindered piperidinoalcohols in accordance with this invention include imidoether salts, usually hydrochlorides, such as formimidoethyl ether hydrochloride $HC(OC_2H_5)=NH_2Cl$; lower alkyl ortho esters such as tributyl orthoformate, triethyl orthoformate, trimethyl orthoacetate and tripropyl orthoformate; and cyclic ortho esters including trihydric alcohol orthoformate esters such as poly(glyceryl orthoformate) and the cage-type trimethylolpropane orthoformate

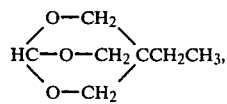

dihydric alcohol ortho esters of the type

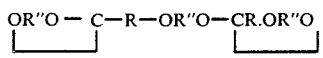

such as triethylenedi-orthoformate, and cyclic ortho esters of the type

such as 2-ethoxy-2-ethyl-1,3-dioxolane and 2-methoxy-5,5-dimethyl-1,3-dioxane.

The reaction of a hindered piperidinoalcohol with a trioxyalkylating agent according to this invention can be represented by equations as in SCHEME 1, as follows:

SCHEME 1

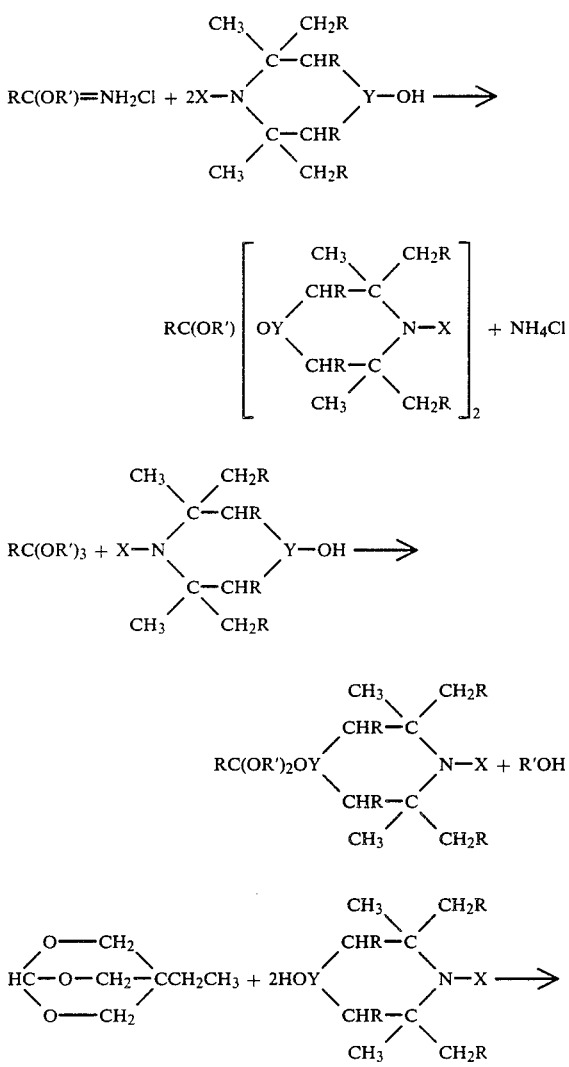

-continued
SCHEME 1

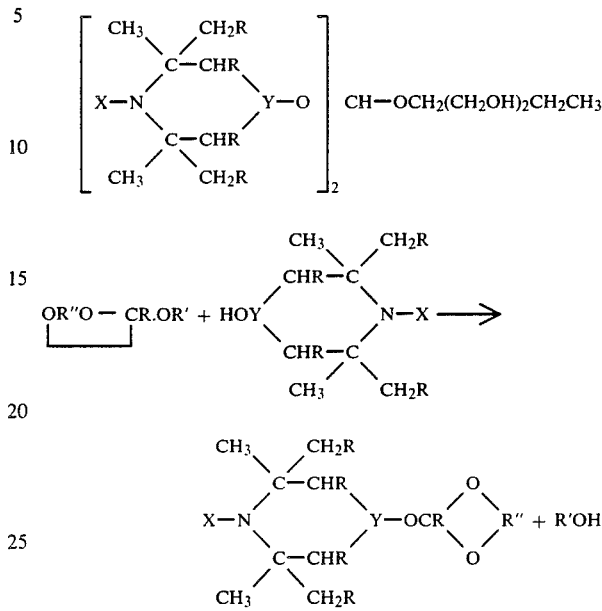

Preferred process conditions for the reaction of the trioxyalkylating agent with the hindered piperidinoalcohol usually include heating the reactants together in the presence of a catalyst. Either reactant can be used in excess to facilitate complete conversion of the other reactant as nearly as possible, the choice of the excess reactant being based on the relative ease of recovery and/or removal of the reactant used in excess. Suitable catalysts include proton acids, Lewis acids, bases, and metallic compounds, examples of which include hydrogen chloride, trifluoromethanesulfonic acid, magnesium chloride, zinc chloride, tributyl borate, aluminum isopropoxide, sodium hydride, potassium carbonate, tribasic lead sulfate, and dimethyltin oxide. Reactants, catalyst, and reaction vessels are preferably kept free of moisture.

In a favorable case the desired product crystallizes from the reaction mixture. Where this does not occur, the mixture can be filtered to remove any solid catalyst residue or neutralized to stop the action of dissolved catalyst, and then distilled, suitably under vacuum, to separate the desired product from volatile by-products and unreacted starting materials. Removal of a volatile by-product such as ethanol can be assisted by heating under a partial take-off condenser in the presence of a solvent boiling at a higher temperature, such as xylene.

Multistage preparations where a hindered piperidinoalcohol reacts with a trioxyalkylating agent to give a 1,1,1-trioxyalkane of this invention having reactive groups which in a subsequent reaction can give a different 1,1,1-trioxyalkane of this invention are diagramed in Scheme 2A and 2B below, using certain trioxymethanes (i.e. orthoformate esters) to illustrate.

SCHEME 2A - HINDERED PIPERIDINOALCOHOL ORTHOFORMATE INTERMEDIATES
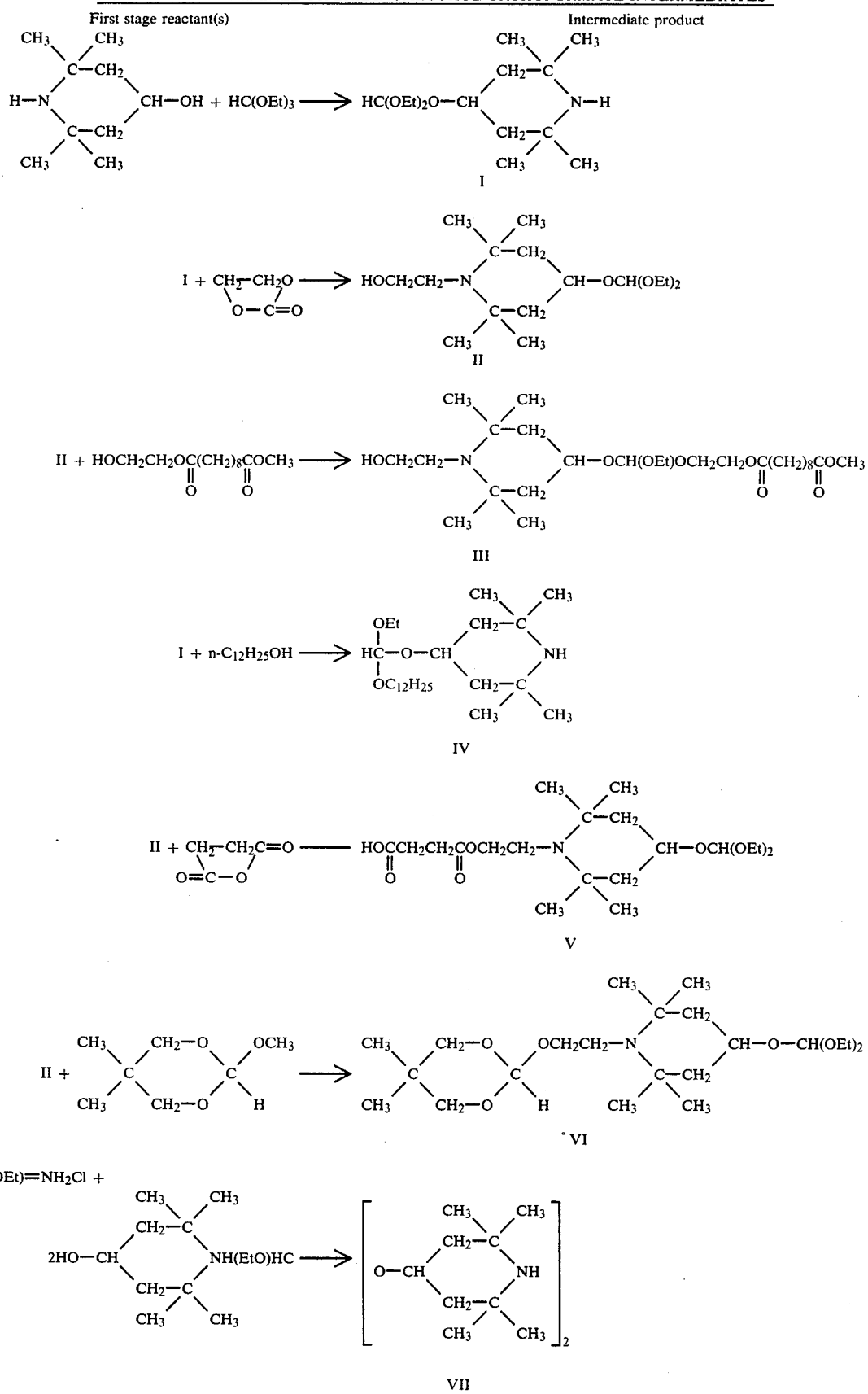

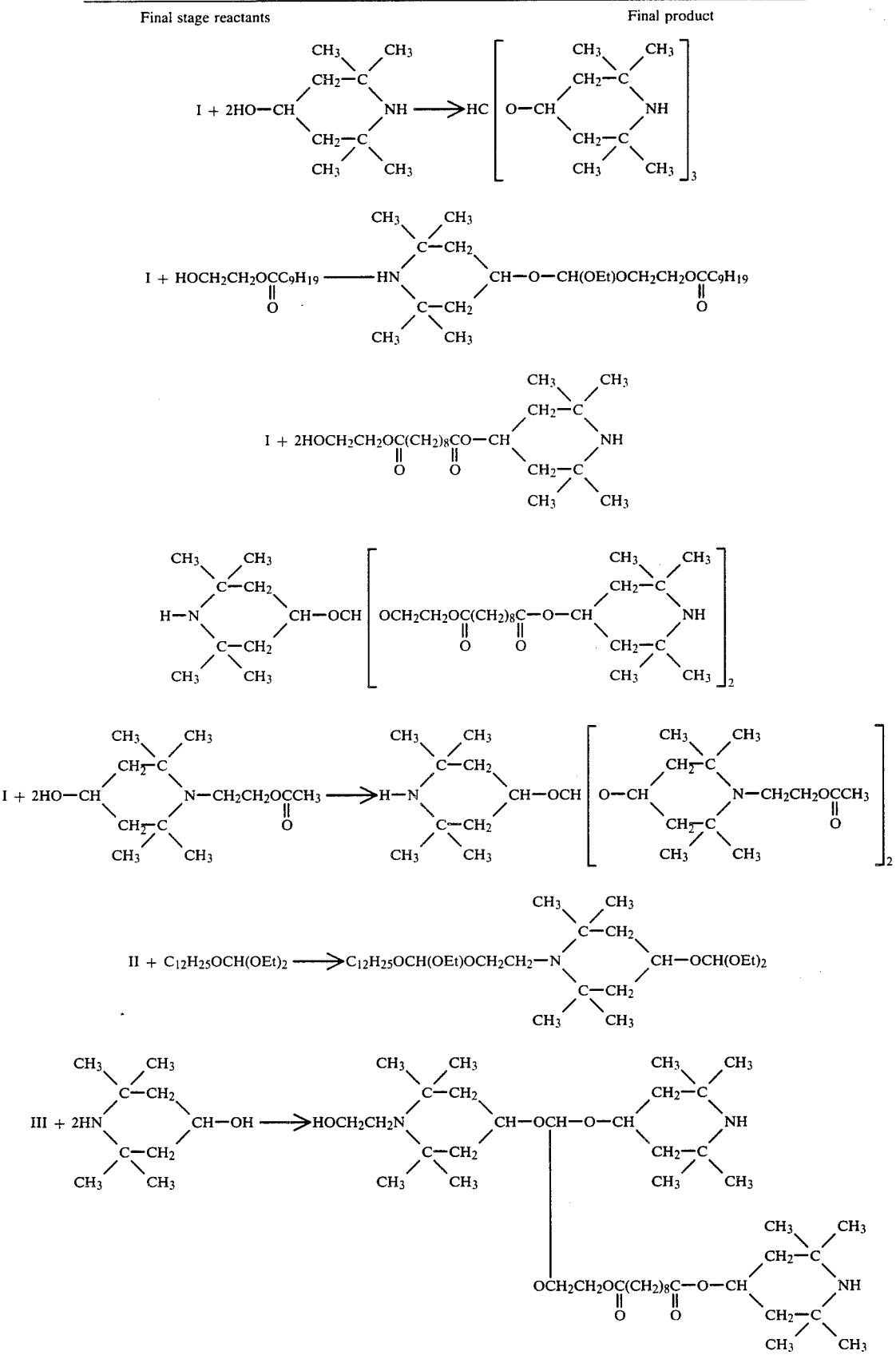

-continued
SCHEME 2B - MULTISTAGE HINDERED PIPERIDINOALCOHOL ORTHOFORMATE PRODUCTS

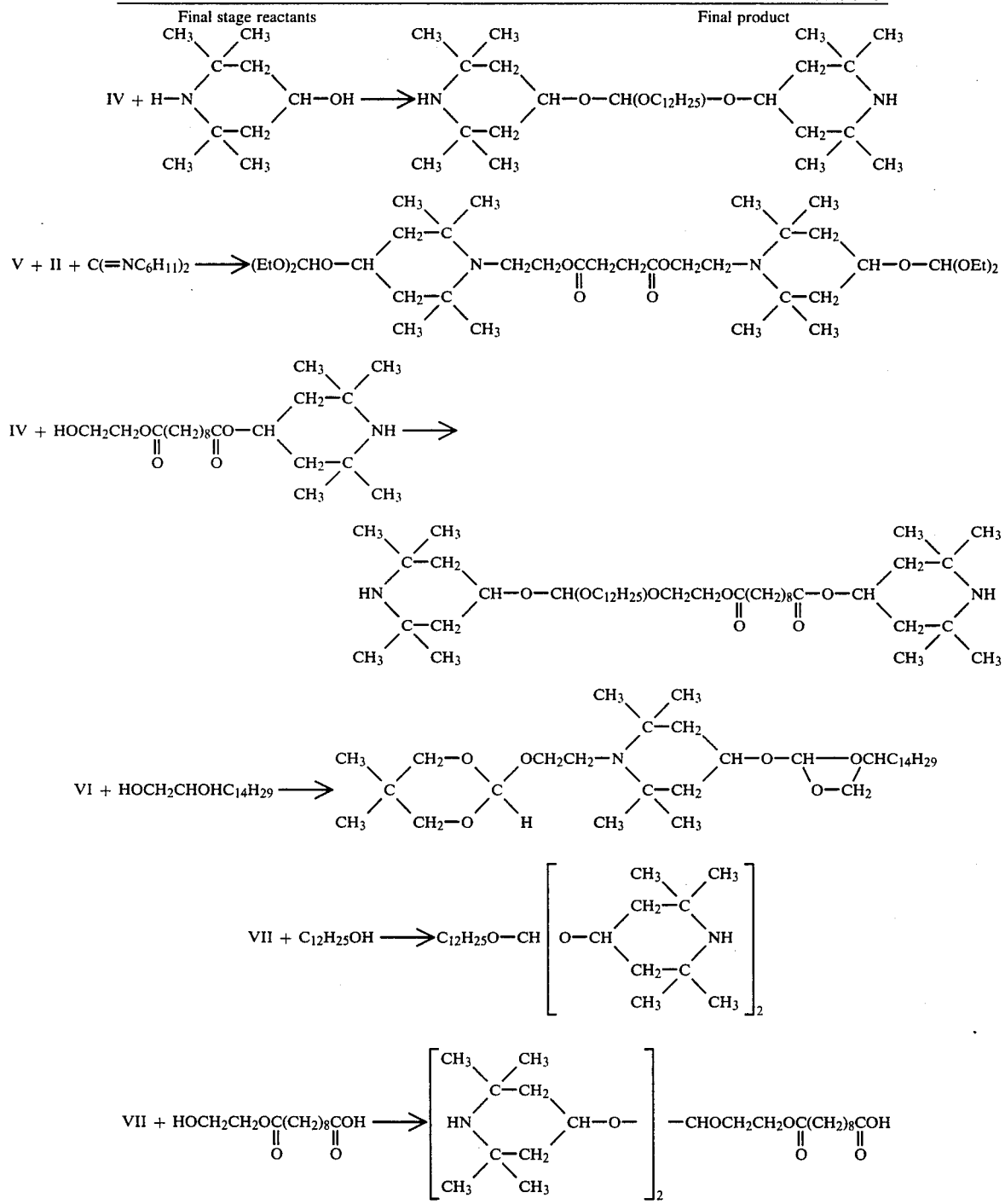

Alcoholic hydroxyl-functional 1,1,1-trioxyalkanes of this invention can furnish additional derivative 1,1,1-trioxyalkane embodiments of this invention by appropriate reaction at the alcoholic hydroxyl group. Illustrative 1,1,1-trioxyalkanes of this invention with an alcoholic hydroxyl group are compounds II and III above. Illustrative derivatives available by reaction at the alcoholic hydroxyl group include trialkylsilanol ethers, formed by reaction with chlorotrimethylsilane and an acid acceptor or with hexamethyldisilazane; borate esters formed by exchange reaction of the hydroxyl-functional orthoformate with a lower alkyl borate, suitably trimethyl borate; carbonate, phosphite, and phosphate esters, formed by carbonating or phosphorylating the alcoholic hydroxyl-functional orthoformate with an ester of carbonic acid or an oxy-acid of phosphorus, i.e. phosphorous acid or phosphoric acid, or a carbonyl halide, chloroformate ester, or phosphorus halide together with an acid acceptor. Carbonating and phosphorylating agents that can be used include diphenyl carbonate, diethyl phosphite, triethyl phosphite, triphenyl phosphite, diphenyl pentaerythritol diphosphite, phosgene, 2-ethylhexyl chloroformate, phosphorus trichloride, neopentylene cyclic chlorophosphite, phosphorus oxychloride, and diphenyl chlorophosphate; the hydrogen halide acceptor used with any of the halogen-containing reagents can be any anhydrous inorganic or organic or organic base including aliphatic, aromatic and heterocyclic tertiary amines, such as trimethylamine, diethylaniline, pyridine, and N-ethylmorpholine, also ammonia gas, sodium metal, sodium hydride, and potassium t-butoxide. To illustrate the formation of representative trioxyalkane silanol ether, borate, carbonate, phosphite, and phosphate derivatives of this invention, reactions of the alcoholic hydroxyl-functional orthoformate ester II of this invention at the alcoholic hydroxyl group are shown in Scheme 3 below.

SCHEME 3-DERIVATIVES OF ALCOHOLIC HYDROXYL-FUNCTIONAL ORTHOFORMATE ESTERS

| Reactants with Compound II | Product |
|---|---|
| bis(trimethylsilyl)acetamide ⟶ | 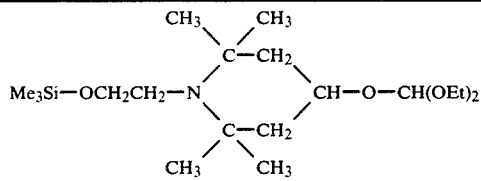 |
| trimethyl borate ⟶ | 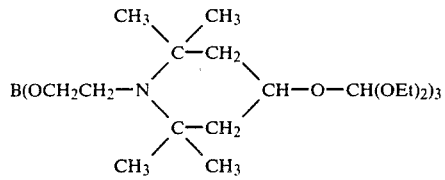 |
| diphenyl carbonate ⟶ | 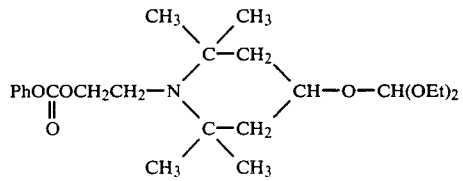 |
| | and |
| 2-ethylhexyl chloroformate + triethylamine ⟶ | 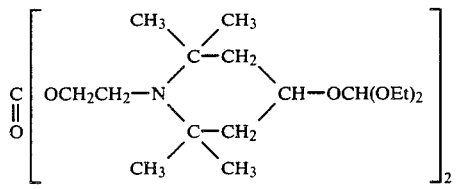 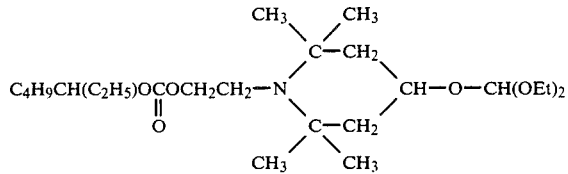 |
| diethyl phosphite ⟶ | 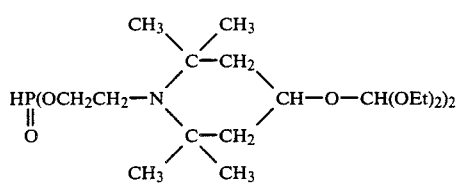 |
| diphenyl penta-erythritol diphosphite ⟶ | 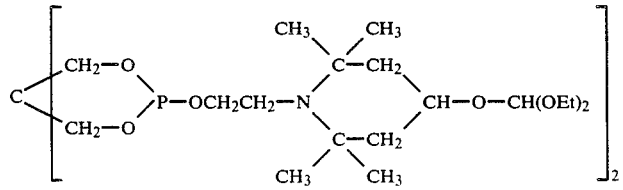 |

SCHEME 3-DERIVATIVES OF ALCOHOLIC HYDROXYL-FUNCTIONAL ORTHOFORMATE ESTERS

| Reactants with Compound II | Product |
|---|---|
| Neopentylene chlorophosphite + triethylamine ⟶ | 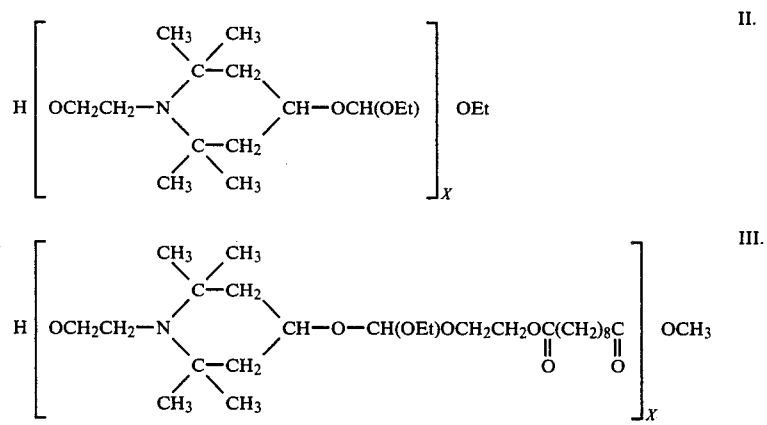 |
| diphenyl chlorophosphate + triethylamine ⟶ | |

Alcoholic hydroxyl-functional 1,1,1-trioxyalkanes of this invention can also furnish oligomers and polymers by interaction of an alcoholic hydroxyl group with an orthoformate ester group as in Compound II or a carboxylic acid ester group as in Compound III. The resulting oligomeric and polymeric materials have particularly favorable properties when incorporated as stabilizers in olefin polymers. The formation of representative trioxyalkane oligomer and polymer derivatives of this invention from the alcoholic hydroxyl-functional orthoformate esters II and III of this invention is shown in Scheme 4 below, where the degree of polymerization X is a number from 2 to about 5.

The oligomer and polymer formation of II is suitably carried out by heating the compound in the presence of a mild acidic or metal compound catalyst under conditions that favor the removal of the ethanol formed in the reaction, suitably under reduced pressure assisted by an inert gas sparge, until the desired degree of polymerization has been obtained. Catalysts include acetic acid, benzoic acid, formic acid, ammonium chloride, magnesium chloride, aluminum and titanium alkoxides, and zinc chloride. Modest and economical catalyst levels from 0.0001% to 1% by weight of the reaction mixture are adequate.

Oligomer and polymer formation of III is carried out by heating the compound in the presence of a catalyst capable of promoting transesterification reactions under conditions that favor the removal of lower molecular weight alkanol formed in the reaction. Any of the catalysts previously recited can be used.

SCHEME 4
POLYMERIC DERIVATIVES OF ALCOHOLIC HYDROXYL-FUNCTIONAL ORTHOFORMATE ESTERS

II.

III.

Formulas of representative 2,2,6,6-tetraalkylpiperidine 4-alcohol 1,1,1-trioxyalkane compounds according to this invention are as shown below.

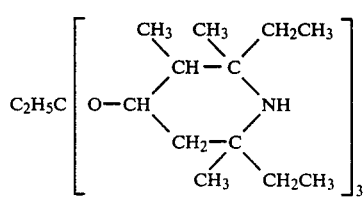  1.

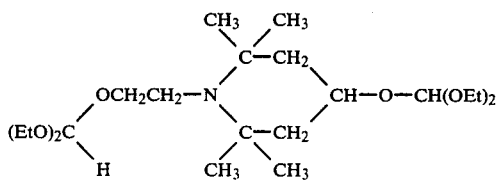  2.

-continued
3. 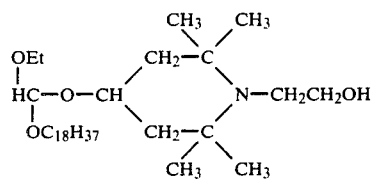
4. 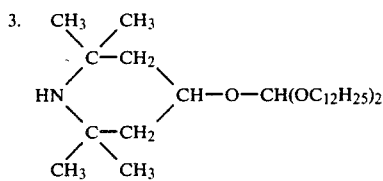
5. 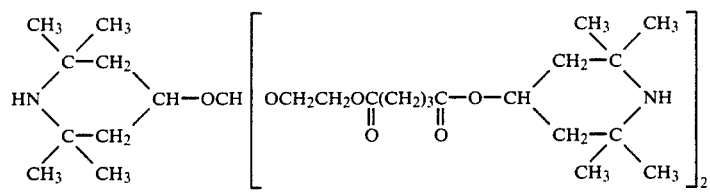
6. 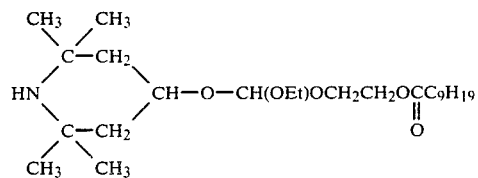
7. 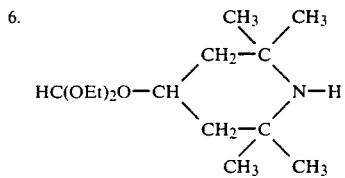
8. 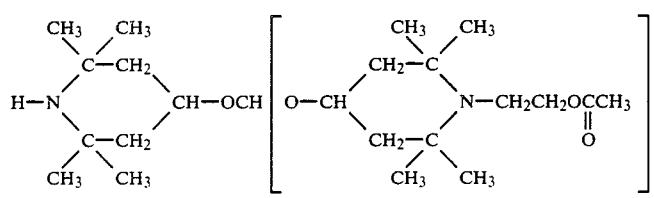
9. 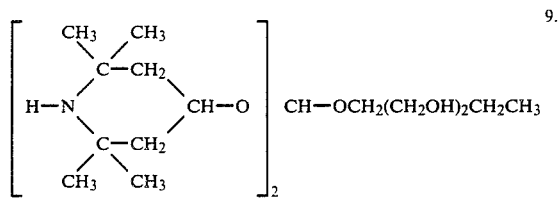
10. 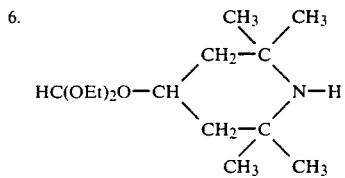
11. 
12. 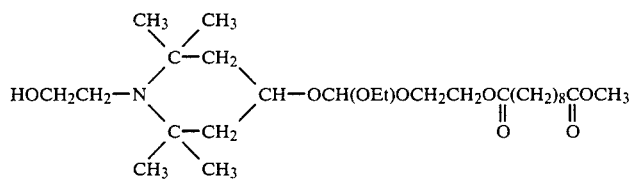
13. 
14. 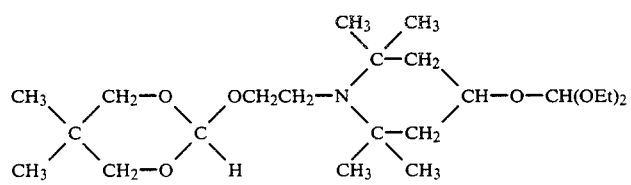

15.
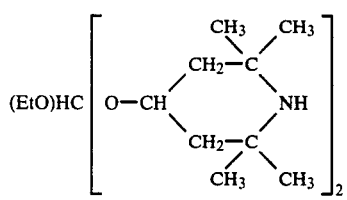
16.
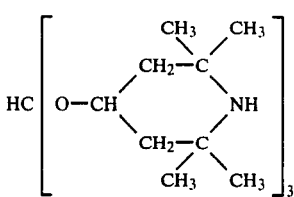
17.
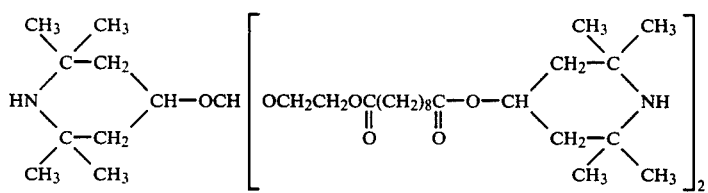
18.
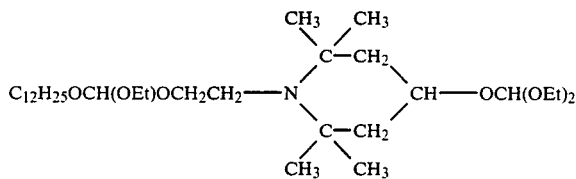
19.
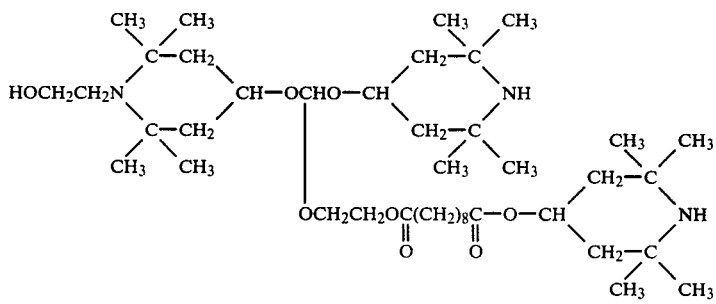
20.
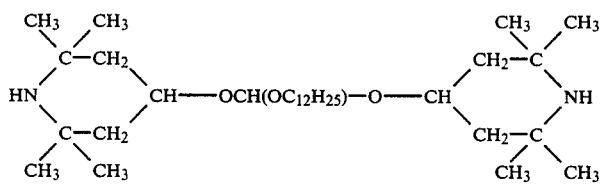
21.
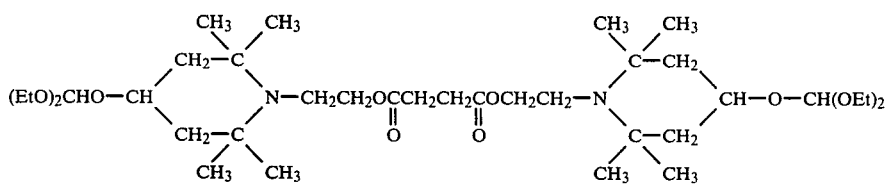
22.
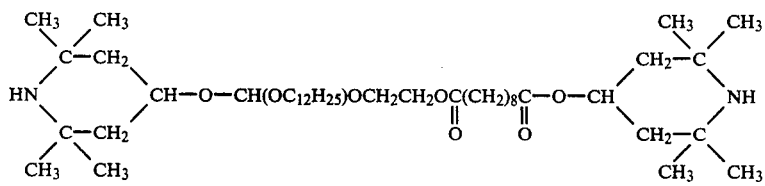
23.
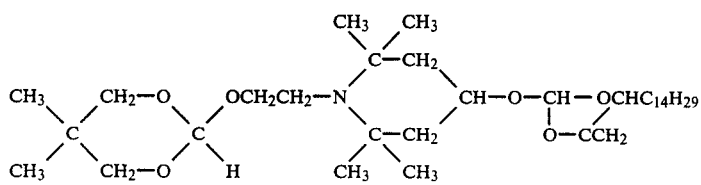

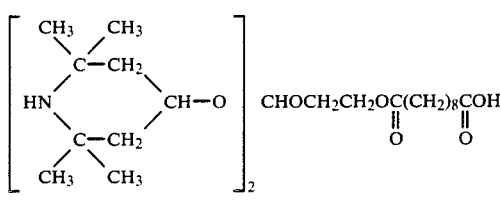 24.
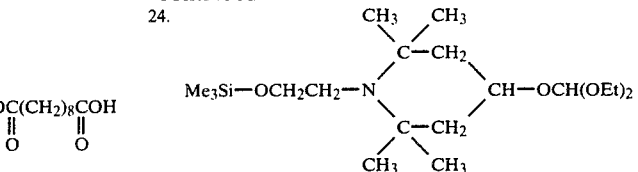 25.

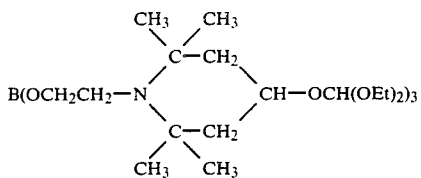 26.
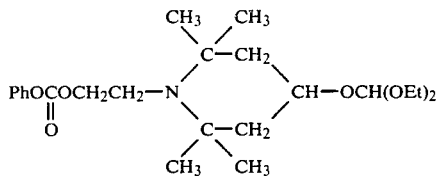 27.

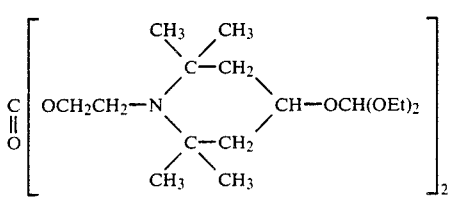 28.
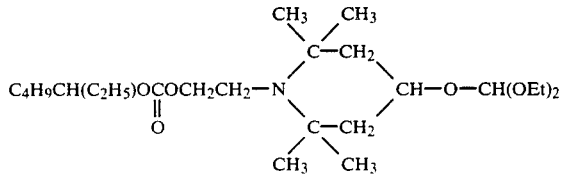 29.

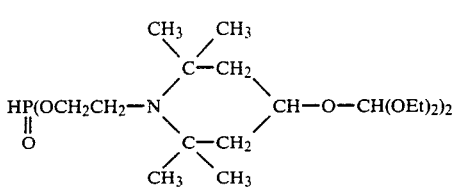 30.
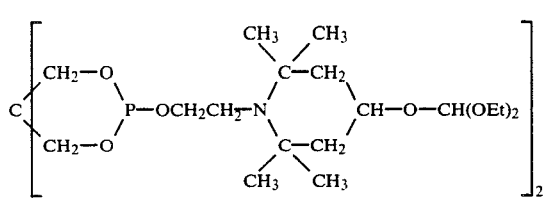 31.

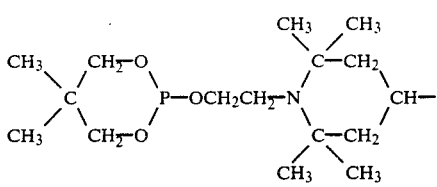 32.
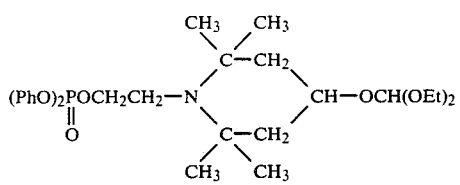 33.

Synthetic resins that can be stabilized with compositions comprising a hindered piperidinoalcohol 1,1,1-trioxyalkane according to this invention include alphaolefin polymers such as low density polyethylene, medium density polyethylene, high density polyethylene, so-called "linear low density" polyethylene (actually a copolymer of ethylene with a minor amount of a higher alphaolefin such as 1-butene, 1-hexene, or 1-octene), polypropylene, polybutene, poly-3-methylbutene, or copolymers thereof such as ethylene-vinylacetate copolymer, ethylenepropylene copolymer, polystyrene, polyvinylacetate, acrylic ester resins, copolymers from styrene and another monomer (for example, maleic anhydride, butadiene, acrylonitrile and so on), acrylonitrilebutadiene-styrene copolymer, acrylic acid ester-butadiene-styrene copolymer, methacrylic acid ester-butadiene-styrene copolymer, methacrylate ester resin such as polymethylacrylate, polyvinylalcohol, ethylene and butylene terephthalate polyesters, diaminoalkane/alkenedicarboxylic and lactam polymer polyamides, polycarbonate, polyacetal, polyurethane, cellulosic resin, or phenolic resin, urea resin, melamine resin, epoxy resin, unsaturated polyester, silicone resin, halogen-containing resins such as polyvinyl chloride, polyvinylidene chloride, polyvinylidene fluoride and copolymers thereof, and further rubbers such as isoprene rubber, chloropreme rubber, and blends of the above resins.

Stabilizer compositions comprising a hindered piperidinoalcohol 1,1,1-trioxyalkane according to this invention can be formulated and marketed in liquid, solid, and paste forms. An inert solvent can be used to facilitate handling. The orthoformate ester and known polymer stabilizers can be solubilized in one another by heating, such as at 70°-160° C., for up to 4 hours, and then allowing the resulting melt to cool and harden sufficiently to be flaked and ground.

Known polymer stabilizers can be used in synthetic resin compositions together with the orthoformate ester stabilizers of this invention and can be admixed with the latter. Such stabilizers include thiodipropionic acid esters, polyvalent metal salts of carboxylic acids, phenolic antioxidants, organic phosphites, 1,2-epoxides, polyhydric alcohols, alkyltin and antimony mercaptides, ultraviolet absorbers and heavy metal deactivators.

Representative phenolic antioxidants include hydroquinone, butylhydroxyanisole, BHT, 2,5-di-t-butylhydroquinone, 2,6-di-t-butylhydroquinone, propyl gallate, 4-t-butylcatechol, 1,1,3-tris(2-t-butyl-4-hydroxy-5-methylphenyl)butane, and the methyl, n-octadecyl, 2,2'-thiobis(ethyl), and pentaerythritol esters of 3,5-di-t-butyl-4-hydroxyphenylpropionic acid. A useful group of phenolic antioxidants is the class of ortho-dihydric phenols. A description of this class in my U.S. Pat. No. 4,269,731 at column 43 lines 16–45 is here incorporated by reference. further disclosure of phenols that can be used in stabilizer compositions according to this invention is incorporated by reference to M. Minagawa et al U.S. Pat. No. 3,849,370 column 16 line 49 to column 21 line 8.

Representative thiodipropionic acid esters include di-n-dodecyl thiodipropionate, dihexadecyl thiodipropionate, distearyl thiodipropionate, n-octyl eicosanyl thiodipropionate and n-octadecyl cyclohexane-1,4-dimethanol thiodipropionate polyester. A comprehensive disclosure of useful thiodipropionate esters by M. Minagawa et al in U.S. Pat. No. 3,869,423, column 17 line 55 to column 19 line 54 is here incorporated by reference. When thiodipropionate esters are used the concentration based on 100 parts of polymer can range from 0.05 to about 0.75 parts by weight.

Representative polyvalent metal salts include zinc, cadmium, calcium, magnesium, barium, strontium and nickel salts of monocarboxylic acids having 6 to 24 carbon atoms, for example zinc benzoate, calcium palmitate, and nickel 2-ethylbutyrate. A comprehensive disclosure of useful metal salts by M. Minagawa et al in U.S. Pat. No. 3,869,423, column 19 line 56 to column 20 line 35 is here incorporated by reference. When metal salts are used the concentration based on 100 parts by weight of polymer can range from 0.1 to about 3 parts by weight.

Representative organic phosphites include triisodecylphosphite, tris(nonylphenyl phosphite), and 4,4'-isopropylidene diphenol alkyl ($C_{12}$–$C_{15}$) phosphite. A comprehensive disclosure of useful organic phosphites in my U.S. Pat. No. 4,269,731 column 43 line 51 to column 47 line 15 is here incorporated by reference. Typical use concentrations of organic phosphites are in the range from 0.02 part to about 2 parts by weight per 100 parts of polymer being stabilized.

Representative 1,2-epoxides that can be used in stabilizer compositions according to this invention include epoxysoybean oil, epoxylinseed oil, and 2-ethylhexyl epoxystearate. A comprehensive disclosure of 1,2-epoxyies by M. Minagawa et al in U.S. Pat. No. 3,869,423 column 26 line 13 to line 39 is here incorporated by reference. Typical use concentrations of 1,2-epoxides range from 0.3 to about 6 parts by weight per 100 parts of synthetic resin composition.

Aliphatic polyhydroxy compounds can be included with stabilizer compositions of this invention in amounts corresponding to 0.1 to about 1 part per 100 parts of polymer being stabilized. Typical aliphatic polyhydroxy compounds are glycerol, polyglycerol, mono-di-, and tri-pentaerythritol, mannitol, sorbitol, and partial esters of these with saturated and unsaturated fatty acids having 6 to 22 carbon atoms.

Alkyltin and antimony mercaptides are characterized by the essential mercaptide group C—S—Sn—C and C—S—Sb— respectively. Tin-linked alkyl groups can be any primary alkyl from methyl to n-octadecyl and even higher if available. The mercaptans from which these mercaptides are derived can be, for example, any of the mercaptocarboxylic acid esters disclosed in my U.S. Pat. No. 4,269,731, in particular at column 12 lines 20 to 34; the mercaptodicarboxylic esters disclosed in my U.S. Pat. No. 4,058,543 (column 4 line 52 to column 11 line 51; the mercapto esters disclosed by L. Brecker in U.S. Pat. Nos. 3,803,083 (see particularly column 3 line 33 to column 6 line 17), 4,256,618 (column 8 line 48 to column 9 line 29), and 4,255,320 (column 11 line 50 to column 12 line 35); the multifunctional mercapto esters disclosed in my U.S. Pat. Nos. 3,115,509 (column 1 lines 35 to 51) and 3,069,447 (column 1 lines 20 to 36) and the mercaptans disclosed by C. Best in U.S. Pat. No. 2,731,484 (column 1 lines 25 to 40). All these disclosures are here incorporated by reference.

Ultraviolet absorbers can be included in stabilizer compositions of this invention in amounts corresponding to 0.05 to about 1 part per 100 parts of synthetic resin being protected. Typical ultraviolet absorbers are 2-hydroxybenzophenones such as 2-hydroxy-4-n-octyloxybenzophenone, 2,4-dihydroxybenzophenone, and 2,2'-dihydroxy-4-n-dodecyloxybenzophenone, and also 2-(2'-hydroxyphenyl)benzotriazoles such as 2-(2'-hydroxy-5'-methylphenyl)benzotriazole, 2-(2'-hydroxy-5'-t-butylphenyl) 5,6-dichlorobenzotriazole, and 2-(2'-hydroxy-5'-tt-octylphenyl)benzotriazole. For a further listing of many useful ultraviolet absorbers the disclosure of U.S. Pat. No. 3,395,112 of July 30, 1968, particularly columns 14 line 40 to column 19 line 33 which are here incorporated by reference, can be consulted.

Stabilizer compositions according to this invention that protect synthetic resin compositions used in contact with materials containing heavy metals and their compounds, as in insulating materials for copper based electrical conductors or in compositions pigmented with heavy metal containing pigments such as rouge, talc, and iron-bearing asbestos, can contain heavy metal deactivators that counteract the prodegradant effect of the heavy metal on synthetic resin compositions that would be satisfactorily stabilized in the absence of heavy metal. Heavy metal deactivators that can be used in stabilizer compositions according to this invention include melamine, dicyandiamide, oxanilide, N,N'-disalicyloylhydrazine, 3-salicyloylamido-1,2,4-triazole, as well as the heavy metal deactivators disclosed by M. Minagawa in U.S. Pat. Nos. 3,549,572 (column 5 line 19 to column 10 line 23), 3,629,181 (column 5 line 15 to column 9 line 54), 3,673,152 (column 4 line 47 to column 8 line 62), and 3,849,370 (column 5 line 5 to column 13 line 45). These disclosures are here incorporated by reference.

EXAMPLE 1

A three-neck flask fitted with stirrer, reflux condenser, thermometer, and surrounded by a heating mantle was charged with a solution containing 48 g (0.3 mole) 2,2,6,6-tetramethylpiperidin-4-ol, 32.2 g (0.22 mole, a significant excess) triethyl orthoformate, 200 cc xylene, and 1.25 g tetrabutyl titanate catalyst. The mixture was heated with stirring, and ethanol started to distill as the solution temperature reached 120° C. Distillation of ethanol continued for approximately 15 hours and the mixture was then heated 8 hours more under reflux. Most of the xylene was then removed under vacuum of 10 mm, leaving an oily solid which was left at ambient temperature to allow for the evaporation of any remaining solvent. The waxy solid 2,2,6,6-tetramethylpiperidin-4-yl orthoformate derivative obtained in 85% yield melted at 120°–130° C. This product was probably a mixture of tris(2,2,6,6-tetramethylpiperidin-4-yl)orthoformate with some ethyl bis(2,2,6,6-tetramethylpiperidin-4-yl)orthoformate and some diethyl 2,2,6,6-tetramethylpiperidin-4-yl orthoformate, so that an accurate molecular weight could not be measured

EXAMPLES 2 AND 3

By using the same method as in Example 1, the following compounds were obtained.

Example 2: oleyl bis(2,2,6,6-tetramethylpiperidin-4-yl)orthoformate and dioleyl 2,2,6,6-tetramethylpiperidin-4-yl orthoformate, from oleyl alcohol, triethyl orthoformate, and 2,2,6,6-tetramethylpiperidin-4-ol.

Example 3: Cyclic ethylene 2,2,6,6-tetramethylpiperidin-4-yl orthoformate, from triethyl orthoformate, ethylene glycol, and 2,2,6,6-tetramethylpiperidin-4-ol.

EXAMPLE 4

A viscous oily oligomer was obtained by heating together 148.2 g triethyl orthoformate (1 mole) plus 20% excess (30 g) with 314.4 g (2 moles) of 2,2,6,6-tetramethylpiperidin-4-ol in 600 cc toluene with 10 g ($\frac{1}{2}$% by weight) of tetrabutyl titanate catalyst under reflux for 20 hours at 90°-100° C. After stripping off side product ethanol under vacuum, 118 g (1 mole) of 1,6-hexanediol was added and heating continued for 15 hours. At the end of this time there was added one mole of bis(2,2,6,6-tetramethylpiperidin-4-yl)ethyl orthoformate (separately prepared from triethyl orthoformate and 2,2,6,6-tetramethylpiperidin-4-ol as described above) and the whole heated 20 hours at 100° C., and then stripped of solvent under vacuum to a final condition of 160° C. and 10 mm. the oligomer product was a viscous light yellow oil and can be represented by the formula

in which pip stands for 2,2,6,6-tetramethylpiperidin-4-yl, and X is a positive number not greater than ten.

EXAMPLE 5

An apparatus similar to that of Example 1 was charged with a solution containing 314.5 g (2 moles) 2,2,6,6-tetramethylpiperidin-4-ol, 192.4 g (1.3 moles) triethyl orthoformate, 150 cc toluene, and 3 g tetrabutyl titanate catalyst. The whole was heated stirring for 20 hours at 90°-100° C. to afford a mixture of 2,2,6,6-tetramethylpiperidin-4-yl diethyl orthoformate pip—O—CH(OC$_2$H$_5$)$_2$ and bis(2,2,6,6-tetramethylpiperidin-4-yl)ethyl orthoformate (pip—O)CHOC$_2$H$_5$, pip representing the 2,2,6,6-tetramethylpiperidin-4-yl group.

EXAMPLE 6

The product of Example 5 was treated with 59 g (0.5 mole) 1,6-hexanediol, heated under reflux for 22 hours at 95°-105° C., and vacuum-stripped to remove the solvent. There was obtained a soft waxy solid 2,2,6,6-tetramethylpiperidin-4-yl, 1,6-hexanediol orthoformate derivative melting at 125°-136° C. This product was probably a mixture of 1,6-hexamethylene-bis(2,2,6,6-tetramethyl-piperidin-4-yl) bis-orthoformate (pip—O)$_2$CHOCH$_2$CH$_2$CH$_2$CH$_2$CH$_2$CH$_2$—OCH(O—pip)$_2$ with some 6-hydroxyhexyl bis-2,2,6,6-tetramethylpiperidin-4-yl)orthoformate and some ethyl bis(2,2,6,6-tetramethylpiperidin-4-yl)orthoformate.

EXAMPLE 7

The operation of Example 5 was repeated with 157.2 g (1 mole) 2,2,6,6-tetramethylpiperidin-4-ol, 270 g (1 mole) 1-octadecanol, 192.4 g (1.3 moles) triethyl orthoformate, 150 cc toluene, and 4 g tetrabutyl titanate catalyst. The resulting product contained 2,2,6,6-tetramethylpiperidin-4-yl ethyl 1-octadecyl orthoformate (pip—O)CH(OC$_2$H$_5$)OC$_{18}$H$_{37}$, the significance of pip being as above.

EXAMPLE 8

One half of the product of Example 7 was treated with 118 g 1,6-hexanediol (1 mole) and one half of the product of Example 5. The whole was processed as in Example 6 to give a waxy solid having a broad melting range and infra-red spectrum consistent with the formula (pip—O)$_2$CHOCH$_2$CH$_2$CH$_2$CH$_2$CH$_2$CH$_2$—OCH(O—pip)OC$_{18}$H$_{37}$ with pip being as above.

EXAMPLE 9

Mono(2-hydroxyethyl)sebacate and 23.6 g (0.1 mole) 1,2,2,6,6-pentamethylpiperidin-4-ol 17.1 g (0.1 mole) were esterified by heating with 0.4 g toluenesulfonic acid catalyst and 100 cc toluene in a reflux apparatus including a Dean-Stark trap to collect the reaction water as it evolved. When no more water obtained 22.2 g (0.15 mole) triethyl orthoformate was added and heating under reflux continued for 9 hours. Stripping under vacuum removed toluene and excess triethyl orthoformate, and left an oily liquid product represented by formula

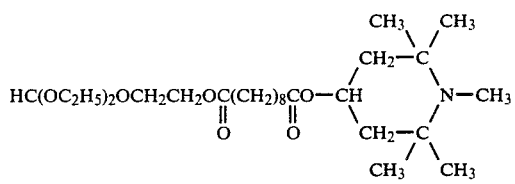

EXAMPLE 10

The product of Example 9 was reacted with 34.2 g (0.2 mole) 1,2,2,6,6-pentamethylpiperidin-4-ol, 0.6 g tetrabutyl titanate catalyst and 150 cc of boiling xylene in an apparatus including a total reflux and partial take-off distillation head that permitted the distillation of ethanol formed in the reaction. After the reaction finished, the mixture was vacuum stripped to remove xylene and leave the product as a viscous oil residue. The product can be represented by the formula

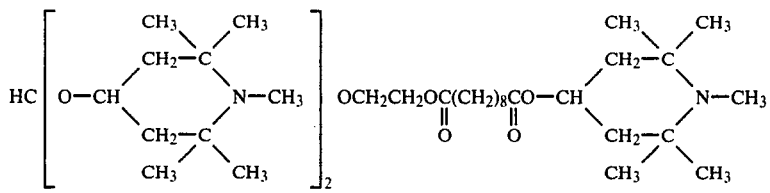

EXAMPLE 11

In an apparatus as in Example 1, a solution containing 48 g (0.3 mole) 2,2,6,6-tetramethylpiperidin-4-ol, 49 g (0.3 mole) 1,1,1-triethoxyethane, 200 cc xylene, and 1.5 g tetrabutyl titanate was stirred and heated as long as ethanol distilled from the mixture (about 15 hours) and 8 hours more at 130°–140° C. Removal of solvent under vacuum left an oil product which was probably a mixture of 1,1-diethoxy 2,2,6,6-tetramethylpiperidin-4-oxyethane and 1-ethoxy-1,1-bis(2,2,6,6-tetramethylpiperidin-4-oxy)ethane.

EXAMPLES 12–15

Compounding and testing of stabilized polypropylene

A commercial homopolymer of propylene supplied as a free-flowing powder with no stabilizer except for about 50 mg/kg of BHT antioxidant (which is only sufficient to prevent deterioration during shipment and storage but not during hot processing or exposure to actinic light) was blended in a high-intensity mixer with calcium stearate acid acceptor, 1000 mg/kg, tetrakis(-methylene(3,5-di-t-butyl-4-hydroxyhydrocinnamate))methane phenolic antioxidant, 1000 mg/kg, and 2000 mg/kg special photo-stabilizing additive as noted below. The resulting powder blend was extruded through a one inch Kilian extruder at 205° C. and pelletized. Pellets from each formulation were molded to provide panels measuring 150×150×0.5 mm which were used for the following tests:

A. High temperature exposure: Five strips cut from each molded panel were exposed in an air circulating oven at 150° C. and examined daily for signs of failure such as surface crazing or embrittlement. The time to failure is the time required for signs of failure to occur in three or more of each group of five strips.

| Sample | Photo-stabilizing additive | Time to Failure Hours |
|---|---|---|
| Control I | None | 576 |
| Control II | bis(2,2,6,6-tetramethylpiperidin-4-yl)sebacate | 360 |
| Control III | Polymeric hindered amine $(C_{26}H_{52}N_4)_n$ n = 1–12 (U.S. Pat. No. 4,104,248) | 360 |
| Example II | Orthoformate ester of Example 6 | 672 |

B. Actinic light exposure: Five strips cut from each molded panel were exposed in a rectangular chamber, placed six inches under a bank of 4 40 watt fluorescent lamps, and examined daily for signs of failure such as surface crazing or embrittlement. The time to failure is the time required for signs of failure to occur in three or more of each group of five strips.

| Sample | Photo-stabilizing additive | Time to Failure (hours) |
|---|---|---|
| Control I | None | 216 |
| Control II | bis(2,2,6,6-tetramethyl-piperidin-4-yl) sebacate | 1500 |
| Control III | Polymeric hindered amine $(C_{26}H_{52}N_4)_n$ n = 1–12 (U.S. Pat. No. 4,104,248) | 1512 |
| Example 12 | Orthoformate ester of Example 6 | 1612 |
| Example 13 | Orthoformate ester of Example 1 | 1574 |
| Example 14 | Orthoformate ester of Example 4 | 1574 |
| Example 15 | Orthoformate ester of Example 8 | 1701 |

The superior light stabilizing effectiveness of the hindered piperidinoalcohol orthoformate esters of this invention is evident from the above data. It is also noteworthy that the Example 6 orthoformate ester of this invention also exhibits enhanced heat stabilizing effectiveness compared to Control I without hindered amine additive, while the conventional hindered amine additives of Control II and Control III detract from the heat stability of the polymer composition.

EXAMPLE 16

Stabilization of impact-resistant polystyrene

A mixing extruder was used to compound an impact-resistant grade of polystyrene with 0.25% by weight of 2(2'-hydroxy-5'-methylphenyl)benzotriazole (a conventional ultra-violet-absorbing stabilizer) and hindered amine type additives as shown below. After four successive passes through the extruder at 220° C. (428° F.) to homogenize the mixture, 0.5 mm thick specimens were molded and exposed in a carbon-arc "fadeometer" operated at 63° C. (145° F.) for 400 hours.

Color (yellowness index YI-2) and percent elongation were measured on unexposed and exposed samples. The results are tabulated.

| | | Unexposed | | Exposed | |
|---|---|---|---|---|---|
| Sample | Hindered amine | $YI^{-2}$ | % Elongation | $YI^{-2}$ | % Elongation |
| Control IV | None | 5 | 60 | 20 | 12 |
| Control V | bis(2,2,6,6-tetramethyl-piperidin-4-yl) sebacate | 5 | 66 | 10 | 16 |
| Control VI | Polymeric hindered amine mol. wt. about 2000 | 6 | 64 | 10 | 22 |
| Example 17 | Orthoformate ester of Example 6 | 3 | 62 | 8 | 27 |

The unexpected advantage of the orthoformate ester of this invention in the photo-stabilization of impact-resistant polystyrene is evident from the results shown.

I claim:

1. A 1,1,1-trioxyalkane compound in which a single carbon atom is linked both to an aliphatic group having one to five carbon atoms or a hydrogen atom, and to three oxygen atoms, each of which is linked to an organic group through carbon and at least one of which is linked to the 4-position of a 2,2,6,6-tetralkylpiperidine group, the compound having at least 12 carbon atoms, at least one 1,1,1-trioxyalkane group, at least one 2,2,6,6-tetraalkylpiperidine group, and 1 to 4 carbon atoms in each alkyl group linked directly to a carbon atom of the piperidine ring of the 2,2,6,6-tetraalkylpiperidine.

2. A 1,1,1-trioxyalkane according to claim 1 having one 1,1,1-trioxyalkane group and three 2,2,6,6-tetralkylpiperidine groups.

3. A 1,1,1,-trioxyalkane according to claim 2 represented by the formula

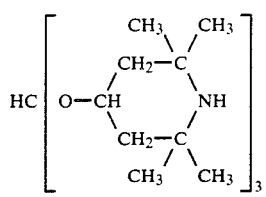

4. A 1,1,1-trioxyalkane according to claim 1 having at least two 1,1,1-trioxyalkane groups.

5. A 1,1,1-trioxyalkane according to claim 4 represented by the formula

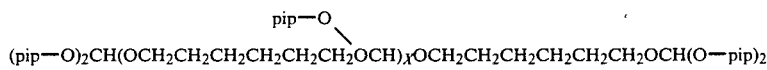

(pip—O)$_2$CH(OCH$_2$CH$_2$CH$_2$CH$_2$CH$_2$CH$_2$OCH)$_x$OCH$_2$CH$_2$CH$_2$CH$_2$CH$_2$CH$_2$OCH(O—pip)$_2$ in which pip is 2,2,6,6-tetramethylpiperidin-4-yl and x is an integer from 0 to 10.

6. A 1,1,1-trioxylakane according to claim 4 represented by the formula (pip—O)$_2$CHOCH$_2$CH$_2$CH$_2$CH$_2$CH$_2$CH$_2$OCH-(O—pip)$_2$ in which pip is 2,2,6,6-tetramethylpiperidin-4-yl.

7. A 1,1,1-trioxyalkane according to claim 4 represented by the formula (pip—O)$_2$CHOCH$_2$CH$_2$CH$_2$CH$_2$CH$_2$CH$_2$OCH-(O—pip)OC$_{18}$H$_{37}$ in which pip is 2,2,6,6-tetramethylpiperidin-4-yl.

8. A 1,1,1-trioxyalkane according to claim 1 represented by the formula

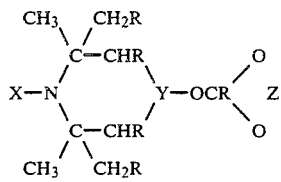

in which independently at each occurrence R is hydrogen or alkyl having 1 to 3 carbon atoms, X is hydrogen, oxyl radical O, alkyl having 1 to 22 carbon atoms, hydroxyalkylene having 2 to 6 carbon atoms, aliphatic acyloxyalkylene having 1 to 22 carbon atoms in the acyl group and 2 to 6 carbon atoms in the alkylene group C$_m$H$_{2m}$O—CH(OR')$_2$ or C$_m$H$_{2m}$O—CH(OR"O); R' is

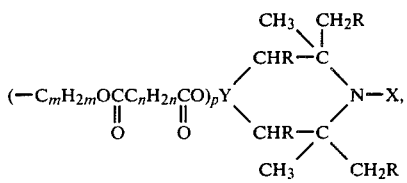

alkyl having 3 to 22 carbon atoms, alkyl having 1 to 22 carbon atoms, hydroxyalkylene having 1 to 2 hydroxyl groups and 2 to 6 carbon atoms, aliphatic acyloxyalkylene having 1 to 22 carbon atoms in the acyl group and 2 to 6 carbon atoms in the alkylene group; R" is alkylene having 2 to 20 carbon atoms; Y is

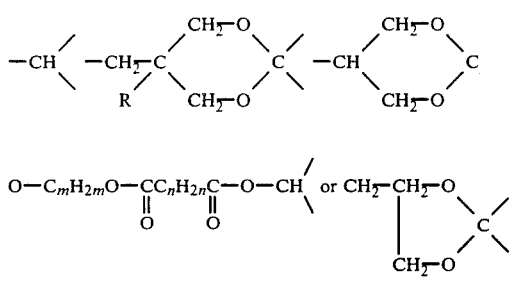

Z is selected from the group consisting of R' groups, R" groups, and

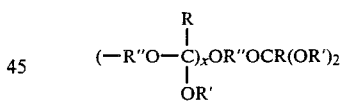

groups taken in sufficient number to satisfy the valences of the two 1,1,1-trioxyalkane oxygen atoms linked to Z; M is an integer from 2 to 10, n is an integer from 0 to 14, p is 0 or 1, and x is an integer from 0 to 10.

9. A 1,1,1-trioxyalkane according to claim 8 in which Y is m=2 and n=8.

10. A 1,1,1-trioxyalkane according to claim 9 represented by the formula

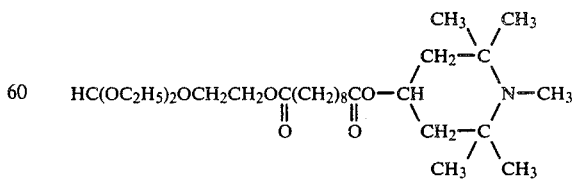

11. A 1,1,1-trioxyalkane according to claim 8 in which R is hydrogen and Y is —CH<.

12. A 1,1,1-trioxymethane according to claim 11 in which X is hydrogen and Z consists of two R' groups.

13. A 1,1,1-trioxymethane according to claim 12 represented by the formula

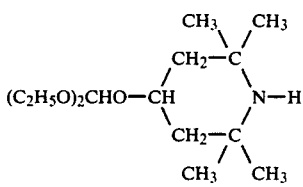

14. A 1,1,1-trioxymethane according to claim 12 in which each R' is n-dodecyl.

15. A 1,1,1-trioxymethane according to claim 12 in which each R' is ethyl.

16. A 1,1,1-trioxymethane according to claim 12 which is 2,2,6,6-tetramethylpiperidin-4-yloxy ethoxy n-octadecyloxymethane.

17. A 1,1,1-trioxymethane according to claim 11 represented by the formula

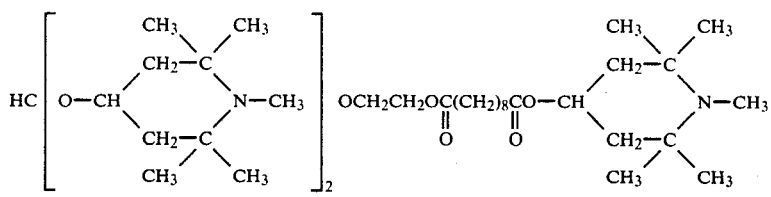

18. A 1,1,1-trioxymethane according to claim 11 in which at least one X is hydrogen and Z consists of

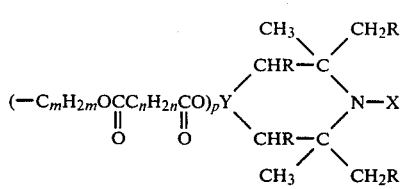

groups.

19. A 1,1,1-trioxymethane according to claim 18 in which p is zero.

20. A 1,1,1-trioxymethane according to claim 19 in which each X is hydrogen.

21. A 1,1,1-trioxymethane according to claim 20 which is ethyl bis(2,2,6,6-tetramethylpiperidin-4-yl)orthoformate.

22. A 1,1,1-trioxymethane according to claim 20 which is oleyl bis(2,2,6,6-tetramethylpiperidin-4-yl)orthoformate.

23. A 1,1,1-trioxymethane according to claim 18 in which $m=2$, $n=8$, and $p=1$.

24. A 1,1,1-trioxymethane according to claim 11 in which at least one X is hydrogen and Z includes exactly one

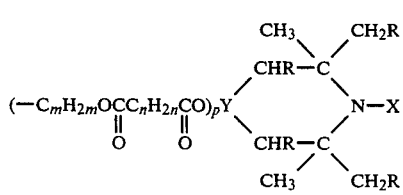

group.

25. A 1,1,1-trioxymethane according to claim 24 in which p is zero and R' is methyl.

26. A 1,1,1-trioxymethane according to claim 24 in which p is zero and R' is n-dodecyl.

27. A 1,1,1-trioxymethane according to claim 24 in which p is zero and R' is hydroxyalkylene.

28. A 1,1,1-trioxymethane according to claim 24 in which p is zero and R' is acyloxyalkylene.

29. A 1,1,1-trioxymethane according to claim 26 in which R' is

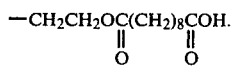

30. A 1,1,1-trioxymethane according to claim 11 in which Z is an R" group.

31. A 1,1,1-trioxymethane according to claim 30 in which R" is 1-hexadecylethylene.

32. A 1,1,1-trioxymethane according to claim 30 in which X is

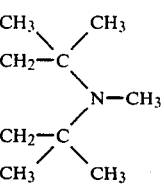

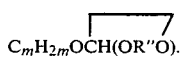

33. A 1,1,1-trioxymethane according to claim 32 in which $m=2$ and R" is ethylene.

34. A 1,1,1-trioxymethane according to claim 32 in which $m=2$ and R" is 2,2,dimethylpropylene.

35. A stabilizer composition capable of increasing the resistance to deterioration on exposure to actinic light of a synthetic resin, comprising an 1,1,1-trioxyalkane according to claim 1 and at least one synthetic resin stabilizer selected from the group consisting of phenolic antioxidants, 1,2-epoxides, antimony and tin mercaptides, organic phosphites, polyhydric alcohols, ultraviolet absorbers, and barium, calcium, cadmium, magnesium, nickel, strontium, tin and zinc salts or monocarboxylic acids having 6 to 24 carbon atoms.

36. A stabilizer composition according to claim 35 comprising a 1,1,1-trialkoxyalkane according to claim 1 and an ultraviolet absorber selected from the group consisting of 2-hydroxybenzophenone compounds and 2-hydroxyphenylbenzotriazole compounds.

37. A stabilizer composition according to claim 35 comprising a 1,1,1-trialkoxyalkane according to claim 1 and a phenolic antioxidant.

38. A stabilized synthetic resin composition comprising a synthetic resin and 0.01 to 2 percent by weight of a 1,1,1-trialkoxyalkane according to claim 1.

39. A stabilized synthetic resin composition according to claim 30 in which the synthetic resin is a polymer of an alphaolefin.

40. A stabilized synthetic resin composition according to claim 38 in which the synthetic resin is a polymer of styrene.

* * * * *